United States Patent [19]

Chorvat et al.

[11] Patent Number: 4,567,270
[45] Date of Patent: Jan. 28, 1986

[54] HEXAHYDROINDOLIZINONES USEFUL FOR TREATING CARDIAC ARRHYTHMIA, THROMBOTIC DISORDERS IN MAMMALS

[75] Inventors: Robert J. Chorvat, Arlington Heights; Kathleen A. Prodan, Buffalo Grove; John A. Schulz, Lindenhurst, all of Ill.

[73] Assignee: G. D. Searle & Co., Skokie, Ill.

[21] Appl. No.: 651,210

[22] Filed: Sep. 17, 1984

[51] Int. Cl.$^4$ .................. C07D 487/00; A61K 31/435
[52] U.S. Cl. .................................. 546/183; 260/244.4; 514/299; 514/212
[58] Field of Search ...................... 546/183; 260/244.4; 514/299, 212

[56] References Cited

U.S. PATENT DOCUMENTS 3,274,202  9/1966  Mohrbacher ........................ 546/183

FOREIGN PATENT DOCUMENTS 127376  10/1981  Japan .................................... 546/183
146772   9/1982  Japan .................................... 546/183

OTHER PUBLICATIONS

L. S. Goodman and A. Gilman, eds., The Pharmacological Basis of Therapeutics (New York, 1980), Sixth Edition, pp. 730–731, 750–751, 761–791, 1360–1361.

P. K. Yonan, "Synthesis and Antiarrhythmic Activity of $\alpha,\alpha$-Bis[(dialkylamino)-alkyl]phenyl acetamides," J. Med. Chem., 23, 1102–1108 (1980).

Primary Examiner—Donald G. Daus
Assistant Examiner—Cecilia Shen
Attorney, Agent, or Firm—Stuart L. Melton; Richard E. L. Henderson

[57] ABSTRACT

This invention relates to hexahydroindolizinones, which are useful as inhibitors of cardiac arrhythmias and of platelet aggregation and are therefore useful in the treatment of irregular heartbeat and in the prevention of thrombus formation.

19 Claims, No Drawings

HEXAHYDROINDOLIZINONES USEFUL FOR TREATING CARDIAC ARRHYTHMIA, THROMBOTIC DISORDERS IN MAMMALS

BACKGROUND OF THE INVENTION (a) Field of the Invention

This invention relates to hexahydroindolizinones, which are useful as inhibitors of cardiac arrhythmias and of platelet aggregation and are therefore useful in the treatment of irregular heartbeat and in the prevention of thrombus formation.

Arrhythmias are disorders relating to electrical impulse generation in the heart. The disorders include premature contractions (extrasystoles) originating in abnormal or ectopic foci in atria or ventricles; atrial flutter; atrial fibrillation; and ventricular tachycardia and fibrillation. For a discussion on these disorders, see, for example, L. S. Goodman and A. Gilman, eds., *The Pharmacological Basis of Therapeutics* (New York, 1980), Sixth Edition, pp. 761–767.

A number of compounds have been developed to alter cardiovascular function related to heart rate and rhythm. The cardiac glycosides, including digitalis, have as their main pharmacodynamic property the ability to increase the force of myocardial contraction. This positive inotropic action is the basis of the salutory effects of these cardiac glycosides in congestive heart failure—increased cardiac output; decreased heart size, venous pressure, and blood volume; and diuresis and relief of edema. See, e.g., Goodman and Gilman at pp. 730–731, 750–751. Quinidine is useful in the therapy of atrial fibrillation but exhibits several toxic reactions, such as cinchonism. Goodman and Gilman at pp. 768–774. Procainamide acts in essentially the same manner as quinidine, and also exhibits toxic side effects. Goodman and Gilman at pp. 774–777. Lidocaine, a widely used local anesthetic, may be used in the treatment of ventricular arrhythmias, but must be administered by injection. Goodman and Gilman at pp. 779–781. Propranolol is useful in the treatment of supraventricular tachycardias and ventricular arrhythmias, but must be used with great care because it may induce significant hypotension, left ventricular failure, or even cardiovascular collapse. Goodman and Gilman at pp. 783–786. Disopyramide has effects somewhat like procainamide and quinidine, all being so-called Type 1 antiarrhythmics. At therapeutic levels disopyramide shortens the sinus node recovery time, lengthens the effective refractory period of the atrium, and has a minimal effect on the refractory period of the A-V node. Goodman and Gilman at pp. 777–779. However, because of the anticholinergic effects of some of the Type 1 antiarrhythmics, such as disopyramide, they should not be used in patients with glaucoma, myasthenia gravis, or problems of urinary retention.

Although part of an important defense mechanism in traumatic injury, thrombus formation can also lead to harmful ischemic or occlusive incidents. Platelet aggregation plays an important part in such thrombus formation. Antithrombotic drugs that reduce the reactivity of circulating hypersensitive platelets may be useful in the prevention and treatment of thrombotic disorders and are particularly advantageous in the prevention of coronary thrombosis associated with myocardial infarction. See, e.g., Goodman and Gilman at pp. 1360–1361. The antiarrhythmic activity of the compounds of the present invention is likewise important in the management of arrhythmias resulting from myocardial infarcts.

(b) Prior Art

As previously described, a number of compounds are useful in the treatment of cardiac arrhythmia. U.S. Application Ser. Nos. 06/532120 filed Sept. 14, 1983 and 06/635,989 filed July 30, 1984 disclose certain antiarrhythmic 1,3-diazabicyclo[4.4.0]decan-4-ones and 1,3-diazabicyclo[4.4.0]dec-2-en-4-ones, each of which has a decalin-like skeleton (i.e., two fused six-membered rings) containing two ring nitrogen atoms, one of which is at a bridgehead position. In contrast, the compounds of the present invention are hexahydroindolizinones (or 1-azabicyclo[4.3.0]nonan-9-ones), each of which has a bicyclic skeleton of fused five- and six-membered rings containing a single ring nitrogen at a bridgehead position. The compounds of Ser. No. '120 and of this invention are further distinguished by the distinctly different locations of substituents around the rings.

SUMMARY OF THE INVENTION

The invention relates to compounds of Formula I:

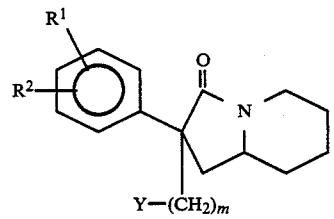

wherein $R^1$ and $R^2$, each being the same or different, are:
(a) hydrogen;
(b) halogen;
(c) alkyl of 1 to 6 carbon atoms, inclusive;
(d) alkoxy of 1 to 6 carbon atoms, inclusive; or
(e) phenyl;

wherein Y is:
(a) $R^3R^4N-$; or
(b) a group of the formula

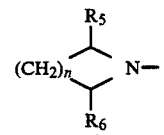

wherein $R^3$ and $R^4$, each being the same or different, are alkyl of 1 to 6 carbon atoms, inclusive; wherein $R^5$ and $R^6$, each being the same or different, are alkyl of 1 to 3 carbon atoms, inclusive; wherein m is an integer from 2 to 6, inclusive; wherein n is an integer from 2 to 4, inclusive; and the racemic mixtures and isomers thereof; and the pharmaceutically acceptable acid addition salts thereof.

Examples of halogen are fluorine, chlorine, and bromine.

Examples of alkyl of 1 to 6 carbon atoms, inclusive, are methyl, ethyl, propyl, butyl, pentyl, hexyl, and the isomeric forms thereof, generally referred to as lower alkyl.

Examples of alkoxy of 1 to 6 carbon atoms, inclusive, are methoxy, ethoxy, propoxy, butoxy, pentoxy, hexoxy, and the isomeric forms thereof.

Examples of pharmacologically acceptable acid addition salts include the hydrochloride, hydrobromide, hydroiodide, sulfate, phosphate, acetate, propionate, lactate, maleate, malate, succinate, and tartrate salts.

DESCRIPTION OF THE INVENTION

The compounds of this invention may be prepared by the method illustrated in Scheme A. Unless otherwise specified, the various substituents are defined as for Formula I, above.

SCHEME A

Under strongly basic anhydrous conditions, various amines of Formula III (in which Y represents a tertiary amino nitrogen and X represents a suitable leaving group, such as halogen, mesylate, or tosylate) will alkylate benzyl nitriles of Formula II to form corresponding nitriles of Formula IV. Preferred alkylating conditions employ chloroalkylamines (Formula III, wherein X is chlorine) and sodamide in toluene at ca. 65°-80°. See P. K. Yonan et al., J. Med. Chem., 23, 1102-1108 (1980). The intermediates, Formula IV, are subsequently alkylated in a similar manner with a 2-halomethylpyridine, Formula V (wherein X' is preferably chlorine), affording compounds of Formula VI.

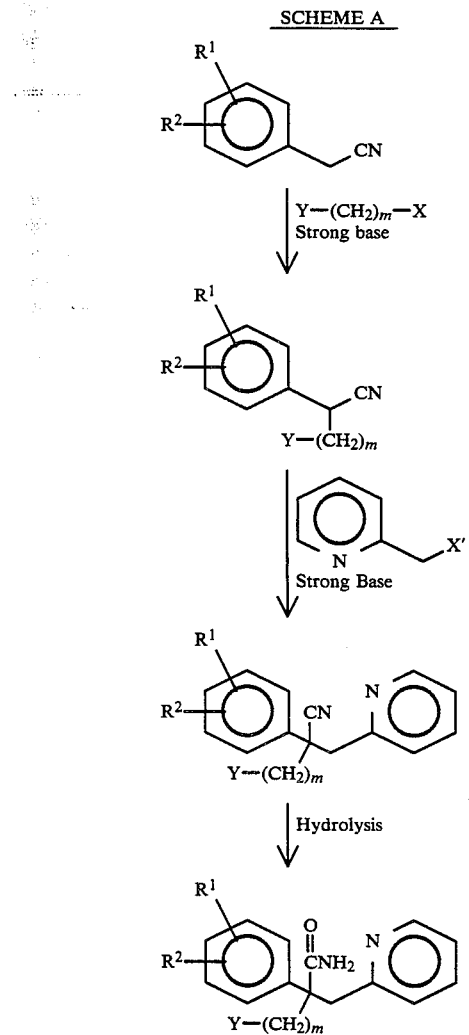

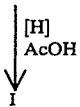

Preferred alkylating conditions employ sodamide or potassium hydride in toluene at ca. 65°-80°. Hydration of intermediate nitriles, Formula VI, yields corresponding amides of Formula VII. Although hydration may be effected in strong acid or base, the preferred methods employ basic hydration in a hot organic solvent. A preferred method uses an alkali metal hydroxide, such as potassium hydroxide, in t-butyl alcohol heated at reflux. Upon reducing the pyridine ring of amides VII, the final ring closure to title compounds of this invention, Formula I, occurs. Preferred reduction conditions include catalytic hydrogenation at room temperature in glacial acetic acid, using hydrogen gas at 60 psi over platinum oxide catalyst. Where cyclization is not completed during reduction, heating the cylized and uncyclized reduction product mixture in a suitable solvent, such as acetone, will give the desired cyclic compounds of Formula I.

The preferred embodiments of this invention include compounds of the following general structure, Formula VIII.

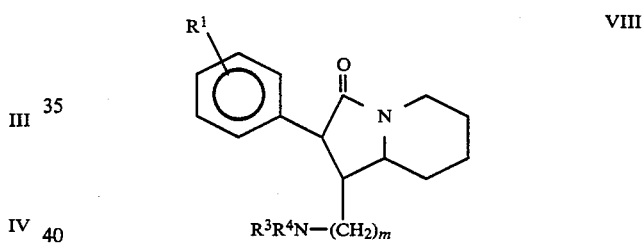

More specifically, the preferred embodiments include compounds of Formula VIII wherein $R^1$ is hydrogen, halogen, or phenyl; wherein $R^3$ and $R^4$, each being the same or different, are alkyl of 1 to 6 carbon atoms, inclusive; and wherein m is 2 or 3.

The most preferred embodiments of this invention include compounds of the following general structure, Formula IX.

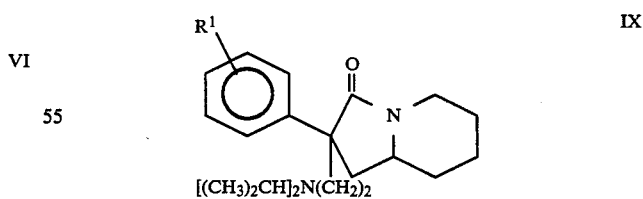

More specifically, the most preferred embodiments include compounds of Formula IX wherein $R^1$ is hydrogen, halogen, or phenyl.

The compounds of this invention exhibited antiarrhythmic activity in dogs in which ventricular arrhythmia was induced by coronary artery ligation. Arrhythmias induced in this manner are considered similar in nature to those resulting from myocardial infarction in humans. Quinidine, procainamide, and disopyramide are active under these conditions and are active in man. The compounds also exhibited antithrombotic activity, as indicated by inhibition of ADP-induced (i.e., non-thromboxane mediated) aggregation of blood platelets. The antiarrhythmic and antiaggregatory activities of the compounds of this invention illustrated in the examples were tested by the following methods.

INHIBITION OF VENTRICULAR ARRHYTHMIA INDUCED BY CORONARY LIGATION

Ventricular arrhythmia was induced by a two-stage ligation of the anterior descending branch of the left coronary artery in each of two or more dogs. Compounds were administered intraveneously using an initial 5 mg/kg body weight dose, with additional doses injected at intervals to a maximum of 20 mg/kg. A compound was rated active if it produced at least a 25% reduction in ectopic beats for a period of at least ten minutes in half or more of the dogs. The average minimum effective dose for each compound was calculated.

Compounds which produced 75-100% reduction in the ventricular arrhythmia at the initial 5 mg/kg dose were further tested using 1 mg/kg doses injected as before at five minute intervals. As before, a compound was rated active if it produced at least a 25% reduction in ectopic beats for a period of at least ten minutes in half or more of the dogs. The average minimum effective dose for each compound was calculated.

Table 1 illustrates the antiarrhythmic activity of certain of the preferred compounds of Formula IX.

TABLE 1
Inhibition of Ventricular Arrhythmia Induced by Coronary Ligation

IX

[(CH$_3$)$_2$CH]$_2$N(CH$_2$)$_2$

| R$^1$ | Minimum Effective Dose (mpk) | Comments |
|---|---|---|
| H | 5.0 | |
| 2-Chloro | 3.0 | Racemate A (Ex. 6) |
| 2-Chloro | 5.0 | Racemate B (Ex. 7) |
| 4-Phenyl | 3.0 | |
| Disopyramide | 9.2 | Human dose (i.v.) ca. 2 mpk |

INHIBITION OF ADP-INDUCED PLATELET AGGREGATION

Optical platelet aggregometry was used to quantitate the extent of platelet aggregation in rat blood plasma. Platelet-rich blood plasma was obtained from rat whole blood containing sodium citrate as anticoagulant. Minimum and maximum light transmittances were determined using platelet-rich plasma and platelet-poor plasma, respectively. Vehicle control response was obtained by adding adenosine diphosphate (ADP), a compound that induces platelet aggregation in blood plasma, to aliquots of platelet-rich plasma in a concentration (usually 1-3 mcM) that gave maximum reversible platelet aggregation within approximately one minute. Test compound responses were determined similarly: Using an initial concentration of $1.0 \times 10^{-4}$M, test compounds were incubated for one minute in platelet-rich plasma and then treated with ADP. Responses were monitored for approximately one minute. A compound was rated active if the mean ADP-induced response was reduced by 50% or more at $10^{-4}$M. For all active compounds, an IC$_{50}$ was determined.

Table 2 illustrates the antiaggregatory activity of certain of the preferred compounds of Formula IX.

TABLE 2
Inhibition of ADP-Induced Platelet Aggregation.

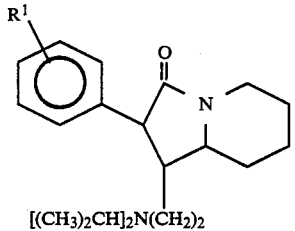

IX

[(CH$_3$)$_2$CH]$_2$N(CH$_2$)$_2$

| R$^1$ | IC$_{50}$ (mcM) | Comments |
|---|---|---|
| H | 81.0 | HCl salt |
| 2-Chloro | 88.0 | Racemate A (Ex. 6) |
| 4-Phenyl | 34.0 | |

By virtue of the antiarrhythmic and antiaggregatory activities, the compounds of Formula I are useful in treating cardiac arrhythmia and in preventing thrombus formation in mammals. A physician or veterinarian of ordinary skill can readily determine whether a subject exhibits either condition. The preferred utility relates to treatment of arrhythmia. Regardless of the route of administration selected, the compounds of the present invention are formulated into pharmaceutically acceptable dosage forms by conventional methods known to those skilled in the art. The compounds may be formulated using pharmacologically acceptable acid addition salts. Moreover, the compounds or their salts may be used in a suitable hydrated form.

The compounds can be administered in such oral dosage forms as tablets, capsules, pills, powders, granules, elixirs, or syrups. They may also be administered intravascularly, intraperitoneally, subcutaneously, or intramuscularly, using forms known to the pharmaceutical art. In general, the preferred form of administration is oral. An effective but non-toxic quantity of the compound is employed in treatment. The dosage regimen for treating arrhythmia or preventing thrombus formation with the compounds of this invention is selected in accordance with a variety of factors, including the type, age, weight, sex, and medical condition of the patient; the severity of the condition; the route of administration; and the particular compound employed. An ordinary skilled physician or veterinarian can readily determine and prescribe the effective amount of the drug required to prevent or arrest the progress of the condition. In so proceeding, the physician or veterinarian could employ relatively low doses at first and subsequently increase the dose until a maximum response is obtained. Dosages of the compounds of the invention, when used in the treatment of arrhythmia, are ordinarily in the range of about 0.1 mg/kg up to about 20 mg/kg. Dosages of the compounds of this invention, when used in the treatment of thrombus formation, are ordinarily in the range of about 1 mg/kg up to about 20 mg/kg.

In the pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug components may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like. Sweetening and flavoring agents and preservatives can also be included where appropriate.

The following examples further illustrate details for the preparation of the compounds of this invention. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted.

DESCRIPTION OF THE PREFERRED EMBODIMENTS

Example 1

α-[2-[bis(1-methylethyl)amino]ethyl]-α-phenyl-2-pyridinepropanenitrile

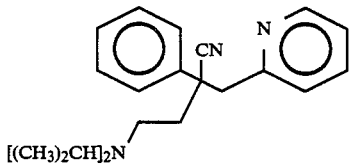

To a solution of 26 g (159 mmole) of 2-picolyl chloride hydrochloride in 50 ml of water was added in portions 22 g (159 mmoles) of potassium carbonate. The solution was extracted into diethyl ether, washed with brine, dried over magnesium sulfate, filtered, and concentrated in vacuo to oily 2-picolyl chloride. A mixture of 29.0 g (119 mmol) of α-[2-[bis(1-methylethyl)amino]ethyl]-phenylacetonitrile and 17.5 g (ca. 153 mmole) of potassium hydride (as a 30% dispersion in mineral oil) was heated for thirty minutes at 65°–70° in 550 ml of toluene. To this mixture was added a solution of the previously prepared 2-picolyl chloride dissolved in 400 ml of toluene. After the reaction mixture was stirred for thirty minutes at 70°, 400 ml of water was added. The toluene layer was separated and extracted with 10% hydrochloric acid. The acidic aqueous layer was separated and made basic with aqueous sodium hydroxide, then extracted with dichloromethane. The organic phase was washed with brine, dried over magnesium sulfate, filtered, and concentrated in vacuo. Column chromatography on silica gel afforded 18.7 g of the title compound as an oil. nmr (CDCl$_3$): δ(ppm) 3.4 (pseudo-d, pyridyl-CH$_2$ (non-equivalent H's)); 6.9–7.7 (m's, aromatic CH's); 8.4–8.6 (m, pyridine 6H).

Example 2

α-[2-[bis(1-methylethyl)amino]ethyl]-α-phenyl-2-pyridinepropanamide

A mixture of 15.0 g (45 mmole) of the title product of Example 1 and 30 g of powdered potassium hydroxide in 180 ml of t-butyl alcohol was heated at reflux overnight. The reaction mixture was poured into water containing sodium chloride, then extracted with dichloromethane. The organic phase was separated, dried over magnesium sulfate, filtered, and concentrated in vacuo to dryness. The crude solid was triturated with diethyl ether and collected by filtration, giving 11.1 g of the title compound as an analytically pure solid.

nmr (CDCl$_3$): δ(ppm) 3.4 (s, pyridyl-CH$_2$); 6.5–6.75 (broad, amide NH$_2$); 6.8–7.5 (m's, aromatic CH's); 8.3–8.5 (m, pyridine 6-H).

Analysis. Calcd. for C$_{22}$H$_{31}$N$_3$O; C, 74.75; H, 8.84; N, 11.89. Found: C, 74.28; H, 8.80; N, 11.77.

Example 3

2-[2-[bis(1-methylethyl)amino]ethyl]-hexahydro-2-phenyl-3(2H)-indolizinone

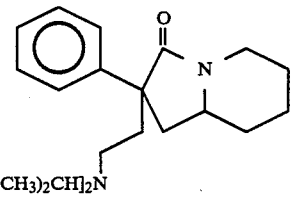

A solution of 11.0 g (31 mmol) of the title product of Example 2 was hydrogenated at room temperature in 200 ml of glacial acetic acid using hydrogen at 60 psi over 1 g of platinum oxide catalyst. After catalyst was removed by filtration, the solvent was removed in vacuo and the residue redissolved in ice/water. The aqueous solution was made basic with dilute aqueous sodium hydroxide and extracted with diethyl ether. The organic layer was washed with brine, dried over magnesium sulfate, filtered, and concentrated in vacuo. Column chromatography on silica gel afforded 5.9 g of the title compound as an analytically pure oil.

nmr (CDCl₃): δ(ppm) 1.1–2.7 (m's, CH₂'s); 4.0–4.3 (broad d, indolizinone bridgehead CH); 6.95–7.6 (aromatic CH's).

Analysis. Calcd. for C₂₂H₃₄N₂O: C, 77.14; H, 10.01; N, 8.18. Found: C, 77.39; H, 10.25; N, 8.41.

Example 4

α-[2-[bis(1-methylethyl)amino]ethyl]-α-(2-chlorophenyl)-2-pyridinepropanenitrile

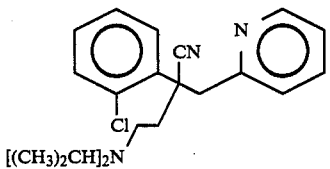

The title compound was prepared by the method of Example 1 using 33 g (118 mmole) of α-[2-[bis(1-methylethyl)amino]ethyl]-2-chlorophenylacetonitrile instead of α-[2-[bis(1-methylethyl)amino]ethyl]-phenylacetonitrile and dimethylformamide at 45°–50° instead of toluene at 65°–70°. After water was added to quench the reaction, the aqueous dimethylformamide solution was extracted with diethyl ether. The organic phase was separated, washed with water, and extracted into dilute aqueous hydrochloric acid. As in Example 1, the aqueous layer was made basic and extracted into dichloromethane, which was then dried and concentrated. The resultant oil was used in subsequent reactions without chromatographic purification. nmr (CDCl₃): δ(ppm) 3.7 (pair of pseudo-d's, pyridyl-CH₂ (isomers, each with non-equivalent H's)); 6.9–7.7 (m's, aromatic CH's); 8.35–8.55 (m, pyridine 6-H).

Example 5

α-[2-[bis(1-methylethyl)amino]ethyl]-α-(2-chlorophenyl)-2-pyridinepropanamide dihydrate

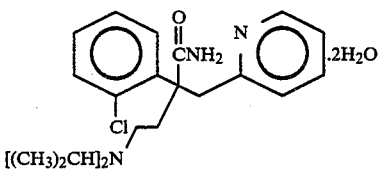

The title compound was prepared as a somewhat impure dihydrate from 43.5 g of the title product of Example 4 using the method of Example 2, except that the initial extraction used diethyl ether instead of dichloromethane and the final trituration used hexane rather than diethyl ether.

nmr (CDCl₃): δ(ppm) 3.6 (pseudo-d, pyridyl-CH₂ (non-equivalent H's)); 6.4–6.65 (broad, amide NH₂); 6.8–7.5 (m's, aromatic CH's); 8.25–8.45 (m, pyridine 6-H)

Analysis. Calcd. for C₂₂H₃₀N₃OCl.2H₂O: C, 62.32; H, 8.08; N, 9.91. Found: C, 62.72; H, 8.08; N, 9.98.

Example 6

2-[2-[bis(1-methylethyl)amino]ethyl]-2-(2-chlorophenyl)hexahydro-3(2H)-indolizinone, Racemate A

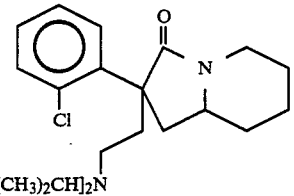

Racemate A

Using the method of Example 3, the title product of Example 5 (6.5 g, 17 mmole) was converted to a mixture of the desired cyclic title compound (Racemates A and B) and the uncyclized piperidine intermediate. The crude solid product mixture was dissolved in acetone and heated at reflux at eight hours. The reaction mixture, upon cooling, was concentrated in vacuo to dryness, redissolved in dichloromethane, dried over magnesium sulfate, filtered, and again concentrated. The resultant oil was chromatographed on silica gel (gradient elution: 100% cyclohexane up to 70:20:2 cyclohexane/isopropyl alcohol/ammonium hydroxide). The more mobile eluate fractions contained the title compound, Isomer A, which was obtained as an analytically pure solid by concentration in vacuo.

nmr (CDCl₃): δ(ppm) 1.1–3.75 (m's, CH₂'s); 4.05–4.4 (broad d, indolizinone bridgehead CH); 7.0–7.45 (aromatic CH's).

Analysis. Calc. for C₂₂H₃₃N₂OCl: C, 70.10; H, 8.82; N, 7.43; Cl, 9.40. Found: C, 70.08; H, 9.06; N, 7.43; Cl, 9.38.

Example 7

2-[2-[bis(1-methylethyl)-amino]ethyl]-2-(2-chlorophenyl)hexahydro-3(2H)-indolizinone, Racemate B

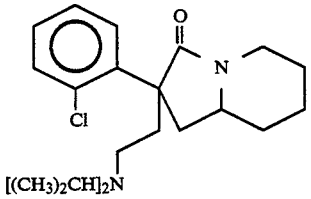

Racemate B

Later eluate fractions of the chromatographic separation of Example 6 afforded the title compound, Racemate B, as an analytically pure solid.

nmr (CDCl₃): δ(ppm) 1.1–3.6 (m's, CH₂'s); 4.0–4.3 (broad b, indolizinone bridgehead CH); 7.0–7.9 (aromatic CH's).

Analysis. Calc. for C₂₂H₃₃N₂OCl: C, 70.10; H, 8.82; N, 7.43; Cl, 9.40. Found: C, 70.03; H, 8.85; N, 7.35; Cl, 9.76.

Example 8

α-[2-[bis(1-methylethyl)amino]ethyl]-α-(4-phenyl-phenyl)-2-pyridinepropanenitrile

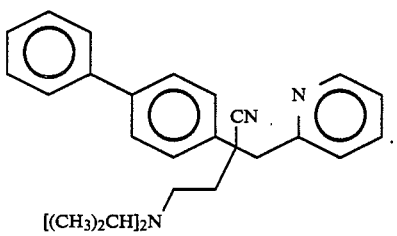

The title compound was prepared as a solid by the method of Example 1 using 16 g (0.05 mole) of α-[2-[bis(1-methylethyl)amino]ethyl]-4-phenyl-phenylacetonitrile instead of α-[2-[bis(1-methylethyl)amino]ethyl]-phenylacetonitrile.

nmr (CDCl$_3$): δ(ppm) 3.45 (pseudo-d, pyridyl-CH$_2$ (non-equivalent H's)); 6.8–7.7 (m's, aromatic CH's); 8.4–8.6 (m, pyridine 6-H).

Example 9

α-[2-[bis(1-methylethyl)amino]ethyl]-α-(4-phenyl-phenyl)-2-pyridinepropanamide

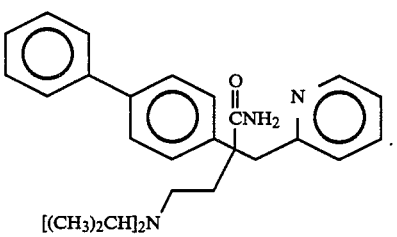

The title compound was prepared from 8.35 g (203 mmole) of the title product of Example 8 using the method of Example 2, except that the initial extraction used diethyl ether instead of dichloromethane.

nmr (CDCl$_3$): δ(ppm) 3.4 (s, pyridyl-CH$_2$ (non-equivalent H's)); 6.65–6.9 (broad, amide NH$_2$); 6.9–7.7 (m's, aromatic CH's); 8.35–8.55 (m, pyridine 6-H)

Analysis. Calcd. for C$_{28}$H$_{35}$N$_3$O: C, 78.28; H, 8.21; N, 9.78. Found: C, 78.25; H, 8.29; N, 9.77.

Example 10

2-[2-[bis(1-methylethyl)amino]ethyl]-2-(4-phenyl-phenyl)hexahydro-3(2H)-indolizinone

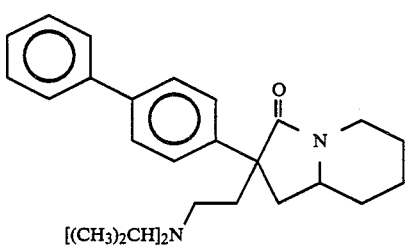

The title compound was prepared from 4 g of the title product of Example 9 using the method of Example 3, except that 0.9 ml of concentrated hydrochloric acid in 250 ml of absolute ethanol was used instead of glacial acetic acid. Instead of using chromatography, recrystallization from aqueous ethanol afforded the title compound as a solid.

nmr (CDCl$_3$): δ(ppm) 4.0–4.4 (broad d, indolizinone bridgehead CH); 7.0–7.7 (aromatic CH's).

Analysis. Calcd. for C$_{28}$H$_{38}$N$_2$O: C, 80.34; H, 9.15; N, 6.69. Found: C, 79.87; H, 9.07; N, 7.32.

Example 11

2-[2-[bis(1-methylethyl)amino]ethyl]hexahydro-2-phenyl-3(2H)-indolizinone hydrochloride hydrate

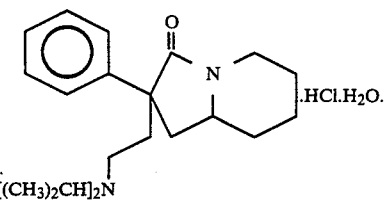

A solution of 24% hydrogen chloride in isopropyl alcohol was added to 6.7 g (18 mmole) of the title product of Example 3 until the mixture remained acidic (ca. pH 2). Addition of diethyl ether produced an oil which was separated. Trituration of the oil with additional diethyl ether induced crystallization of the title compound as an analytically pure hydrochloride hydrate, m.p. 93°–97°

Analysis calcd. for C$_{22}$H$_{34}$N$_2$O.HCl.H$_2$O: C, 66.56; N, 9.39; N, 7.06. Found: C, 66.91, H, 9.30; N, 7.09.

Example 12

2-[2-(2,6-dimethyl-1-piperidinyl)ethyl]hexahydro-2-phenyl-3(2H)-indolizinone

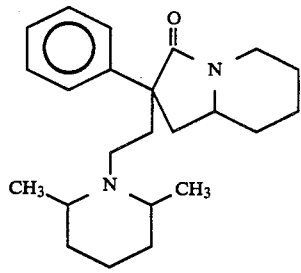

The title compound is prepared by the methods of Examples 1, 2, and 3 using α-[2-(2,6-dimethyl-1-piperidinyl)ethyl]phenylacetonitrile instead of α-[2-[bis(1-methylethyl)amino]ethyl]phenylacetonitrile.

What is claimed is:

1. A compound of the formula:

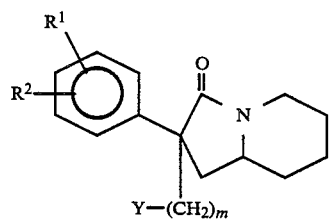

wherein R$^1$ and R$^2$, each being the same or different, are:

(a) hydrogen;
(b) halogen;
(c) alkyl of 1 to 6 carbon atoms, inclusive;
(d) alkoxy of 1 to 6 carbon atoms, inclusive; or
(e) phenyl;

wherein Y is:
(a) R³R⁴N—; or
(b) a group of the formula

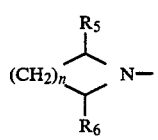

wherein R³ and R⁴, each being the same or different, are alkyl of 1 to 6 carbon atoms, inclusive; wherein R⁵ and R⁶, each being the same or different, are alkyl of 1 to 3 carbon atoms, inclusive; wherein m is an integer from 2 to 6, inclusive; wherein n is an integer from 2 to 4, inclusive; and the racemic mixtures and isomers thereof; and the pharmaceutically acceptable acid addition salts thereof.

2. A compound according to claim 1 having the formula:

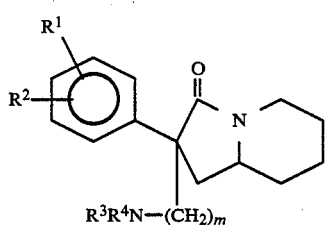

3. A compound according to claim 2 having the formula:

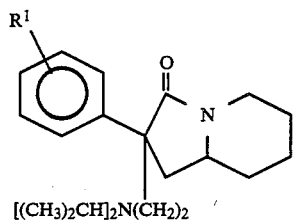

4. A compound according to claim 3, which is 2-[2-[bis(1-methylethyl)amino]ethyl]hexahydro-2-phenyl-3(2H)-indolizinone.

5. A compound according to claim 3, which is 2-[2-[bis(1-methylethyl)amino]ethyl]-2-(2-chlorophenyl)-hexahydro-3(2H)-indolizinone.

6. A compound according to claim 3, which is 2-[2-[bis(1-methylethyl)amino]ethyl]-2-(4-phenylphenyl)-hexahydro-3(2H)-indolizinone.

7. A compound according to claim 1 having the formula:

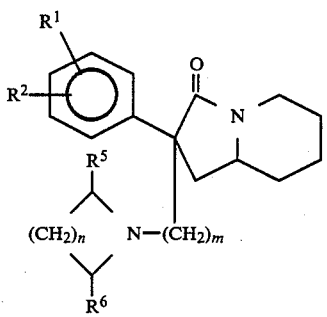

8. A compound according to claim 7 having the formula:

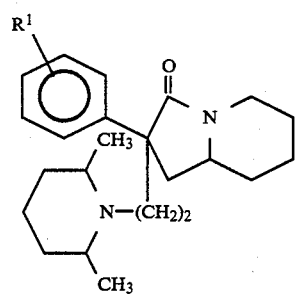

9. A compound according to claim 8, which is 2-[2-(2,6-dimethyl-1-piperidinyl)ethyl]hexahydro-2-phenyl-3(2H)-indolizinone.

10. A pharmaceutical composition for treating cardiac arrhythmia, thrombotic disorders in mammals comprising an effective amount of at least one compound according to claim 1, together with one or more non-toxic pharmaceutically acceptable carriers.

11. A pharmaceutical composition for treating cardiac arrhythmia, thrombotic disorders in mammals according to claim 10 wherein said compound is of the formula:

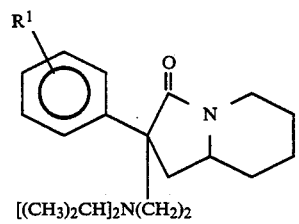

12. A method for treating cardiac arrhythmias in mammals comprising administering a therapeutically effective amount of at least one compound of claim 1 to a mammal in need of such treatment.

13. A method according to claim 12 wherein said compound is of the formula:

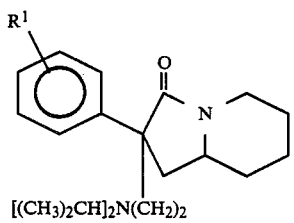

[(CH₃)₂CH]₂N(CH₂)₂

14. A method for treating cardiac arrhythmias in mammals comprising administering a therapeutically effective amount of a pharmaceutical composition of claim 10 to a mammal in need of such treatment.

15. A method for treating cardiac arrhythmias in mammals comprising administering a therapeutically effective amount of a pharmaceutical composition of claim 11 to a mammal in need of such treatment.

16. A method for treating thrombotic disorders in mammals comprising administering a therapeutically effective amount of at least one compound of claim 1 to a mammal in need of such treatment.

17. A method according to claim 16 wherein said compound is of the formula:

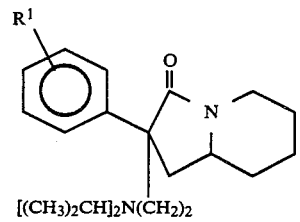

[(CH₃)₂CH]₂N(CH₂)₂

18. A method for treating thrombotic disorders in mammals comprising administering a therapeutically effective amount of a pharmaceutical composition of claim 10 to a mammal in need of such treatment.

19. A method for treating thrombotic disorders in mammals comprising administering a therapeutically effective amount of a pharmaceutical composition of claim 11 to a mammalian patient in need of such treatment.

* * * * *